(12) United States Patent
Reyes

(10) Patent No.: US 12,290,243 B2
(45) Date of Patent: May 6, 2025

(54) DENTAL MIRROR CLEANER

(71) Applicant: Hari Reyes, Ridgefield, WA (US)

(72) Inventor: Hari Reyes, Ridgefield, WA (US)

( * ) Notice: Subject to any disclaimer, the term of this patent is extended or adjusted under 35 U.S.C. 154(b) by 106 days.

(21) Appl. No.: 17/495,484

(22) Filed: Oct. 6, 2021

(65) Prior Publication Data
US 2023/0105258 A1  Apr. 6, 2023

(51) Int. Cl.
A61B 1/12 (2006.01)
A61B 1/247 (2006.01)

(52) U.S. Cl.
CPC .............. A61B 1/125 (2013.01); A61B 1/247 (2013.01)

(58) Field of Classification Search
CPC ... A61B 1/125; A61B 1/24–253; A61C 17/02; A61C 17/0202; A61C 17/088
USPC ........................................................ 433/31
See application file for complete search history.

(56) References Cited

U.S. PATENT DOCUMENTS 2,984,009 A * 5/1961 Codoni .................. A61B 1/253
433/30
3,032,879 A * 5/1962 Lafitte .................... A61B 1/247
385/116
4,279,594 A * 7/1981 Rigutto .................. A61B 1/253
433/95
4,629,425 A * 12/1986 Detsch ................... A61B 1/253
433/29
4,925,391 A * 5/1990 Berlin ................. A61C 17/0202
433/31
5,951,284 A * 9/1999 Lake ...................... A61C 17/08
433/31
2005/0074719 A1* 4/2005 Croop .................... A61B 1/253
433/30
2012/0021373 A1* 1/2012 Moreno ............... A61C 17/088
433/31
2022/0386860 A1* 12/2022 Ramot ................... A61B 1/253

FOREIGN PATENT DOCUMENTS

DE          29705997 U1 *  5/1997 ............. A61B 1/253

* cited by examiner

Primary Examiner — Edward Moran
Assistant Examiner — Matthew P Saunders
(74) Attorney, Agent, or Firm — Mark S. Hubert

(57) ABSTRACT

A dental mirror cleaner that utilizes a spray of high pressure water and air at an angle across the reflective face of a dental mirror while in a patient's mouth to clean debris, blood and condensation from the mirror. It redirects the flow of the water and or air away from the centerline or linear axis of the mirror handle and sprays it offset from this centerline in a hemispherical pattern at an approximate 35 to 45 degree angle across the mirrored face.

5 Claims, 4 Drawing Sheets

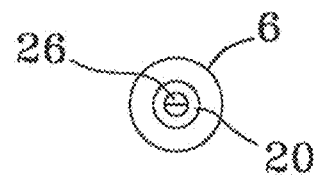
FIG. 4
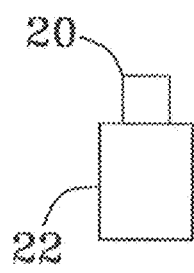 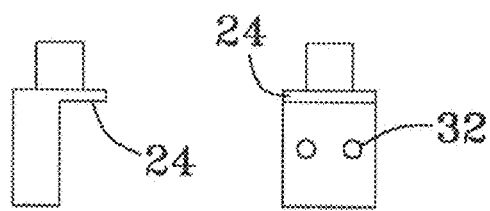 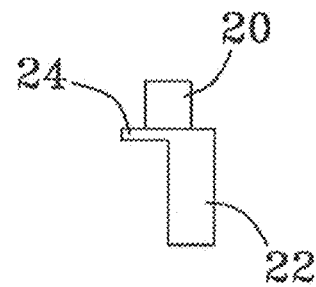
FIG. 5  FIG. 6  FIG. 7  FIG. 8
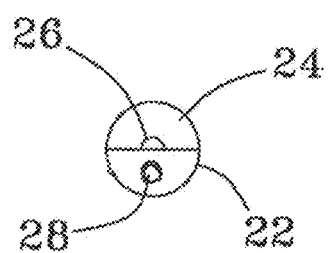
FIG. 9

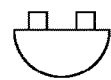
FIG. 10
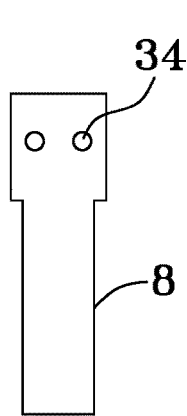 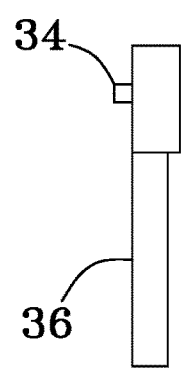 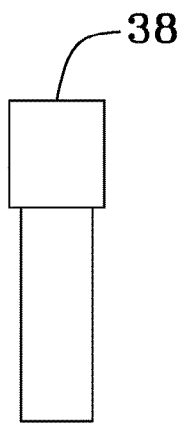 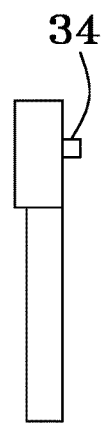
FIG. 11  FIG. 12  FIG. 13  FIG. 14
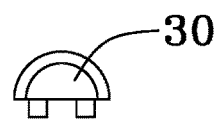
FIG. 15

DENTAL MIRROR CLEANER

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

FIELD

The present disclosure relates, in general, to dentistry, and more particularly to the technology of cleaning of tools used in oral cavities.

BACKGROUND

When a dentist or dental technician performs work deep in a patient's mouth, generally an angled dental mirror is used. These have several inherent drawbacks. Blood, debris, water and fog accumulate on the top reflective face of the mirror. This causes the removal and cleaning of the mirror, the reinsertion and alignment of the mirror and the refocusing of the dentist's vision through his magnifying eyepiece. While certain substances on the mirror can remain somewhat unobtrusively on the mirror, other like blood because of its quick coagulation time, cannot.

The dentist usually has a tool in both hands, such that a dirty mirror necessitates a dental assistant taking control of the mirror and cleaning it. If the mirror is only fogged with condensation, it still requires the dentist to momentarily stop work until the fog evaporates off of the mirror. All told, a dirty or fogged mirror costs the dentist hours of lost time each week. While a dental assistant can spray water and then air onto a mirror while the dentist works, it is very hard to precisely target the moving target of an angled mirror while in in a patient's mouth. Additionally, the dental assistant is usually handing the dentist tools at the same time.

Henceforth, a device that can clean debris, blood and condensation off of a dental mirror with pressurized water and or air while remaining in a patient's oral cavity would fulfill a long felt need in the dental industry. This new invention utilizes and combines known and new technologies in a unique and novel configuration to overcome the aforementioned problems and accomplish this.

BRIEF SUMMARY

In accordance with various embodiments, a dental mirror cleaner is provided.

In one aspect, a dental mirror cleaner that can spray pressurized water and/or air onto an angled dental mirror at the correct angle to completely clear the debris, blood or condensation off of the top reflective face of the mirror, is provided.

In another aspect, a dental mirror cleaner that has a handle barrel, mirror and cleaning media diverter plug that can be sterilized and reused, as well as a replaceable cleaning media spray tube, is provided.

In yet another aspect, a dental mirror cleaner that redirects the flow of pressurized water and air from the handle barrel into a media spray channel that sprays the mirror at the correct angle to completely clean debris, blood and condensation from the top face of the mirror.

Various modifications and additions can be made to the embodiments discussed without departing from the scope of the invention. For example, while the embodiments described above refer to particular features, the scope of this invention also includes embodiments having different combination of features and embodiments that do not include all of the above described features.

BRIEF DESCRIPTION OF THE DRAWINGS

A further understanding of the nature and advantages of particular embodiments may be realized by reference to the remaining portions of the specification and the drawings, in which like reference numerals are used to refer to similar components.

FIG. 4 is a proximal end view of the diverter plug;

FIGS. 5-8 are top, right side, bottom left side views of the diverter plug;

FIG. 9 is a distal end view of the diverter plug;

FIG. 10 is a proximal end view of the media spray tube;

FIGS. 11-14 are top, right side, bottom left side views of the media spray tube; and FIG. 15 is a proximal end view of the media spray.

DETAILED DESCRIPTION OF CERTAIN EMBODIMENTS

Reference will now be made in detail to embodiments of the inventive concept, examples of which are illustrated in the accompanying drawings. The accompanying drawings are not necessarily drawn to scale. In the following detailed description, numerous specific details are set forth to enable a thorough understanding of the inventive concept. It should be understood, however, that persons having ordinary skill in the art may practice the inventive concept without these specific details and that the described examples are provided for illustrative purposes and are not intended to limit the scope of the invention.

It will be understood that, although the terms first, second, distal and proximal, front and back, etc. may be used herein to describe various elements or sections thereof, these elements should not be limited by these terms. These terms are only used to distinguish one element or section thereof from another. For example, a first attachment could be termed a second attachment, and, similarly, a second attachment could be termed a first attachment, without departing from the scope of the inventive concept.

As used herein, the term "water and air spray syringe" refers to a device external to the dental mirror cleaner, that injects air and water into the handle barrel of the device to clean the mirror.

As used herein the term "handle barrel" refers to the structure that resides between the water and spray syringe and the diverter plug and channels pressurized air and/or water to the media spray tube.

As used herein, the term "media" refers to the air, water and air/water combination that is provided by the water and air syringe to the dental mirror cleaner.

The present invention relates to a novel design for a dental mirror cleaner that functions to allow the dentist to instantaneously clean the top face of his dental mirror with a water and air spray syringe while it remains in the oral cavity of the patient. The time savings for the dentist is expected to in the range of 15 minutes per patient.

Figure 1:
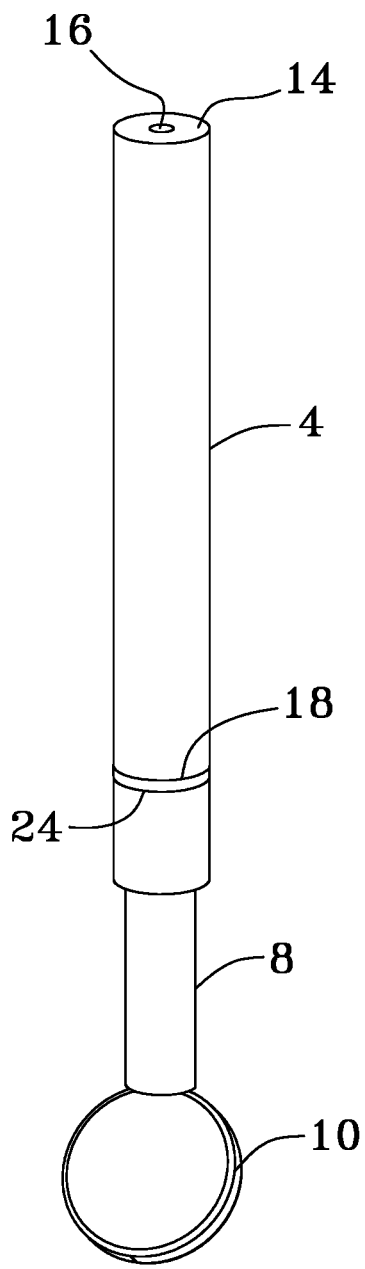
FIG. 1 is a front view of the dental mirror cleaner.
Figure 2:
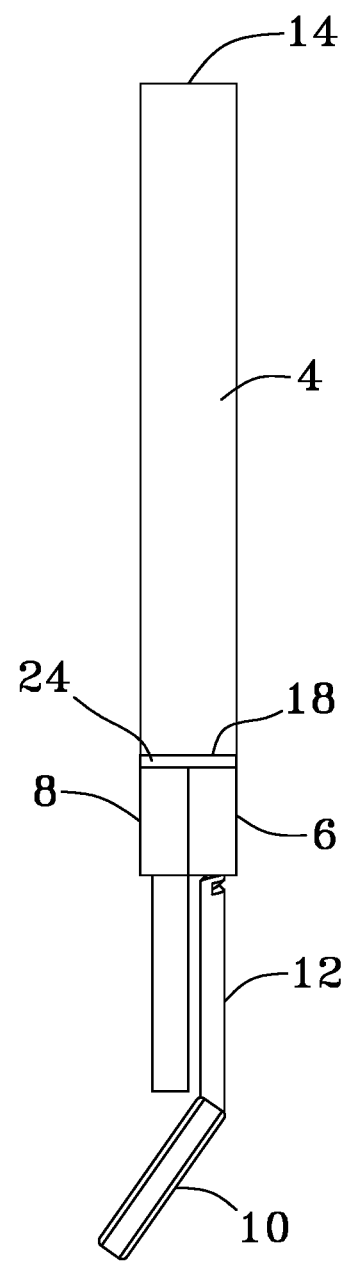
FIG. 2 is a right side view of the dental mirror cleaner.
Figure 3:
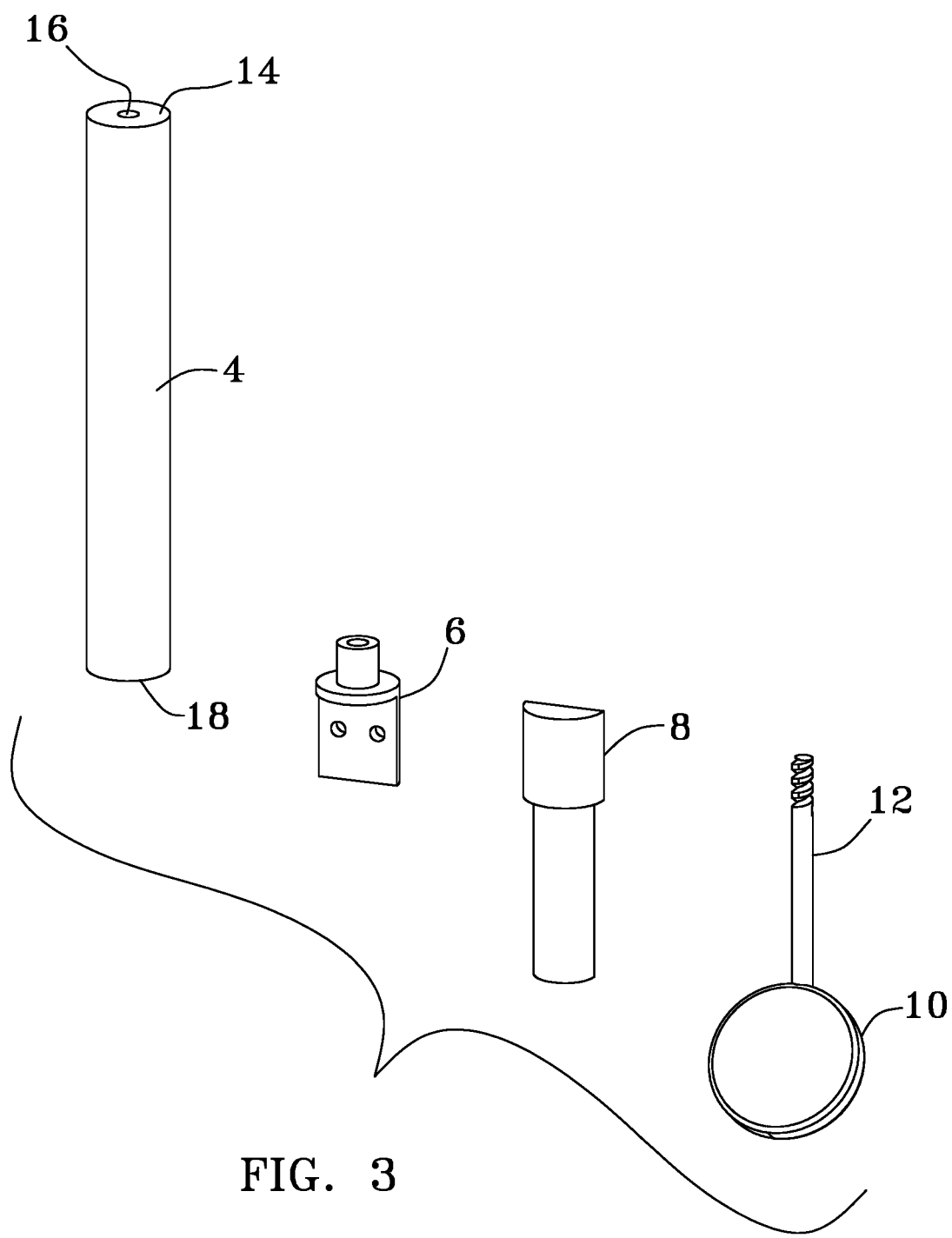
FIG. 3 is a side perspective view of all of the disassembled components of the dental mirror cleaner.

Looking at FIGS. 1, 2 and 3 it can be seen that the dental mirror cleaner 2 consists of a handle barrel 4, a diverter plug 6, a media spray tube 8 and an attachable mirror 10 with an extension arm 12 extending therefrom. Onto the media inlet end 14 of the handle barrel 4 a conventional water and air spray syringe (not shown but well known in the art) may be attached. The handle barrel 4 and the mirror body 10 is stainless steel while the diverter plug 6 and the media spray tube 8 are made from a polymer, preferably polypropylene or a thermoplastic elastomer (TPE).

The handle barrel 4 is a tubular member having a media inlet end 14, a media outlet end 18 and an internal media channel 16 (preferably 4 mm in diameter) formed therebetween its two ends. Onto the media inlet end 14, a water and air syringe device may be removably coupled. This is a device commonly found in all dental offices and capable of spraying media (water, air or a water and air mixture). When operatively coupled to the media inlet end, it allows the user to spray media down the internal media channel 16 to the media outlet end 18 where it may travel through the diverter plug 6 and media spray tube 8 so as to spray across the face of the angled mirror 10. The handle barrel 4 may be sterilized in a conventional dental autoclave. Preferably, it is made of a stainless steel and preferably has the internal media channel 16 running along the first linear axis of the handle barrel 4. Into the internal media channel 16 at the media outlet end of the handle barrel 4 the diverter plug 6 is frictionally engaged.

The diverter plug 6 is best explained with FIGS. 4-9. Here it can be seen that the diverter plug 6 has an engagement stub 20 (preferably circular in cross section), a media spray tube connecting adapter 22 and a sealing flange 24 formed at their interface, therebetween. A media bore 26 is formed between the distal and proximal end of the diverter plug 6. The engagement stub 20 is sized for mating engagement with the internal media channel 16 in the media outlet end 18 of the handle barrel 4. When the diverter plug 6 is coupled to the handle barrel 4, the sealing flange 24 abuts the media outlet end 18, and the second linear axis of the media bore 26 is in fluid communication with, but offset from, the first linear axis of the internal media channel 16. This offset redirection of the media stream is necessary to have the media travel down the semi-circular media spray channel 30 of the media spray tube 8, and strike the angled mirror 10 at the correct angle to quickly clean and clear the mirror 10. A threaded recess 28 is formed into the end face 30 of the media spray tube connecting adapter 22 that accepts the threaded extension arm 12 of a stock mirror 10.

The media bore 26 in the preferred embodiment is a half circular bore so as to move the spray flow of the media into a similarly shaped semi-circular media spray channel 30 that runs inside of the media spray tube 8, with a third linear axis, offset from the first linear axis. On the media spray tube connecting adapter 22 there is a first half mechanical connector 32 that engages a second half mechanical connector 34 on the media spray tube 8 in a plane perpendicular to the second linear axis. (See FIG. 14) When engaged, these two mechanical connectors attach the media spray tube 8 to the diverter plug 6 in a leak proof manner that is able to withstand the approximate 80 psi pressure generated by the water and air spray syringe. Preferably, the second half mechanical connector 34 is a protrusion such as a posts or tabs and the first half mechanical connector 32 is a straight or tapered recesses or slots that is sized for mating engagement. Preferably the media spray tube 8 is made of a polymer with a Durometer Shore A Hardness Scale of 80 to allow elastic deformation of the posts or tabs while connecting the two components.

The media spray tube 8 is a linear member that when connected to the diverter plug 6, resides offset from the first linear axis of the handle barrel 4. This allows the water and air that is sprayed down the dental mirror cleaner 2 to strike the face of the mirror 10 at approximately 35-45 radial degrees. The media spray tube 8 is of a stepped linear configuration that has a semi-circular cylindrical body with a common planar face 36 thereon. At its larger diameter proximal end 38, there is the second half mechanical connector 34 formed thereon.

The media spray tube 8 and the diverter plug 6 may be made of a polymer and disposable while the handle barrel 4, the mirror 10 and mirror extension arm 12 are made of an autoclavable material, preferably stainless or a plated steel. Optionally, the diverter plug 6 may be made of an autoclavable material and thus only the media spray tube 8 need be made disposable.

In operation, the diverter plug 6 and the media spray tube 8 are joined together via the first and second mechanical connectors to form a first leak proof seal. The engagement stub 20 of the diverter plug 6 is frictionally engaged into the media outlet end 18 of the handle barrel 4 until the sealing flange 24 abuts the media outlet end 18 of the handle barrel 4 forming a second leak-proof seal. This second leak-proof seal is accomplished because of a dual seal formed between the engagement stub 20 and the internal media channel 16 and between the sealing flange 24 and the media outlet end 18. The extension handle 12 of the mirror 10 is threadingly engaged into the threaded recess 28 formed into the end face 30 of the media spray tube connecting adapter 22. Lastly, water and air spray syringe is connected to the media inlet end 14 of the handle barrel. Either water, air or water and air are sprayed down the aligned channels of the various components of the device 2 until they exit the media spray tube 8 and strike the top reflective face of the mirror 10 at an angle preferably between 35 and 45 degrees so as to remove debris, blood and condensation from the mirror. This quick cleaning eliminates the need to remove the mirror from the patient's mouth and the need for a dentist to have to refocus their eyes to begin work again. Conservative studies show that this device 2 should be able to save approximately 15 minutes per patient.

While certain features and aspects have been described with respect to exemplary embodiments, one skilled in the art will recognize that numerous modifications are possible. Device components described according to a particular structural architecture may be organized in alternative structural architectures and/or incorporated within other described devices. Hence, while various embodiments are described with—or without—certain features for ease of description and to illustrate exemplary aspects of those embodiments, the various components and/or features described herein with respect to a particular embodiment can be substituted, added, and/or subtracted from among other described embodiments, unless the context dictates otherwise. It will be appreciated that the invention is intended to cover all modifications and equivalents within the scope of the following claims.

Having thus described the invention, what is claimed as new and desired to be secured by Letters Patent is as follows:

1. A dental mirror cleaning device, for cleaning a dental mirror, comprising:

an autoclavable handle barrel with a single internal media channel formed from opposite ends of said handle barrel, said handle barrel having a media inlet end and a media outlet end, said single internal media channel sharing a first linear axis with said handle barrel;

a cleaning media diverter plug having a circular proximal end forming a circular sealing flange with an engagement stub extending therefrom, and a semi-circular distal end with a media bore formed there between said ends, said media bore having a second linear axis, and wherein said media bore is in fluid communication with said single internal media channel of said handle barrel when said engagement stub is frictionally engaged in said media outlet end of said handle barrel and said circular sealing flange abuts said media outlet end, a replaceable cleaning media spray tube with at least one first half mechanical connector protrusion on a planar inner face having a pair of cylindrical locking pegs extending therefrom that are engageable in at least one second half mechanical connector recess of a pair of locking sockets formed into said cleaning media diverter plug in a direction perpendicular to said second linear axis of said media bore, said cleaning media spray tube having a media spray channel formed there along, said media spray channel having a third linear axis that is not colinear with said first linear axis of said handle barrel, but that is colinear with said second linear axis of said media bore of said cleaning media diverter plug; and an autoclavable dental mirror having a planar face residing between 35 and 45 degrees to said third linear axis, said mirror secured by threaded engagement with a threaded bore in said distal end of said cleaning media diverter plug.

2. The dental mirror cleaning device of claim 1, comprising;

a first seal formed by the abutment of said sealing flange of said cleaning media diverter plug and with a proximal end of said cleaning media spray tube; and a dual, second seal formed between said engagement stub of said cleaning media diverter plug and said internal media channel of said handle barrel, and between said media outlet end of said handle barrel and said sealing flange on said cleaning media diverter plug.

3. A dental mirror cleaning device, comprising:

an autoclavable handle barrel with an internal media channel having a media inlet end and a media outlet end; an internal media channel formed along a first linear axis of said handle barrel;

a cleaning media diverter plug having a circular proximal end, a semi-circular distal end with a planar face, and a media bore with a second linear axis formed therebetween in fluid communication with said internal media channel of said handle barrel when said proximal end is frictionally engaged in said media outlet end of said mirror handle barrel;

a recess formed in said distal end of said cleaning media diverter plug for the engagement of an autoclavable dental mirror with a planar face;

a cleaning media spray tube affixable to said cleaning media diverter plug planar face and having a media spray channel formed there along that has a third linear axis that is colinear with a second linear axis of said media bore of said cleaning media diverter plug, and that resides at an angle between 35 and 45 degrees with respect to said planar face of said mirror and said cleaning media spray tube has a pair of cylindrical locking pegs thereon that matingly engage a pair of locking sockets formed into said planar face of said cleaning media diverter plug to ensure a fluid sealing between said media diverter plug and said media spray channel.

4. The dental mirror cleaning device of claim 3, further comprising; a sealing flange at said proximal end of said cleaning media diverter plug that abuts said media outlet end of said handle barrel.

5. The dental mirror cleaning device of claim 4 wherein said third linear axis of said cleaning media converter plug is offset from said first linear axis of said handle barrel.

* * * * *